US012383512B2

(12) United States Patent
Guy et al.

(10) Patent No.: US 12,383,512 B2
(45) Date of Patent: Aug. 12, 2025

(54) CANNABIDIOL-TYPE CANNABINOID COMPOUND

(71) Applicant: Jazz Pharmaceuticals Research UK LImited, Kent (GB)

(72) Inventors: Geoffrey Guy, Cambridge (GB); Volker Knappertz, Cambridge (GB); Benjamin Whalley, Cambridge (GB); Marie Woolley-Roberts, Cambridge (GB)

(73) Assignee: JAZZ PHARMACEUTICALS RESEARCH UK LIMITED, Sittingbourne (GB)

( * ) Notice: Subject to any disclaimer, the term of this patent is extended or adjusted under 35 U.S.C. 154(b) by 618 days.

(21) Appl. No.: 17/777,681

(22) PCT Filed: Nov. 18, 2020

(86) PCT No.: PCT/GB2020/052942
§ 371 (c)(1),
(2) Date: May 18, 2022

(87) PCT Pub. No.: WO2021/099781
PCT Pub. Date: May 27, 2021

(65) Prior Publication Data
US 2023/0000789 A1 Jan. 5, 2023

(30) Foreign Application Priority Data
Nov. 21, 2019 (GB) ..................................... 1916974

(51) Int. Cl.
*A61K 31/05* (2006.01)
*A61K 36/185* (2006.01)
*A61P 25/08* (2006.01)
(52) U.S. Cl.
CPC ............ *A61K 31/05* (2013.01); *A61K 36/185* (2013.01); *A61P 25/08* (2018.01)
(58) Field of Classification Search
CPC .... A61K 31/05; A61K 36/185; A61K 31/658; A61P 25/08; C07C 29/143; C07C 39/23; C07C 2601/16
See application file for complete search history.

(56) References Cited

U.S. PATENT DOCUMENTS

| | | | |
|---|---|---|---|
| 6,630,507 B1 | 10/2003 | Hampson et al. |
| 8,632,825 B2 | 1/2014 | Velasco Diez et al. |
| 8,790,719 B2 | 7/2014 | Parolaro et al. |
| 9,017,737 B2 | 4/2015 | Kikuchi et al. |
| 9,125,859 B2 | 9/2015 | Whalley et al. |
| 9,474,726 B2 | 10/2016 | Guy et al. |
| 9,949,936 B2 | 4/2018 | Guy et al. |
| 9,949,937 B2 | 4/2018 | Guy et al. |
| 9,956,183 B2 | 5/2018 | Guy et al. |
| 9,956,184 B2 | 5/2018 | Guy et al. |
| 9,956,185 B2 | 5/2018 | Guy et al. |
| 9,956,186 B2 | 5/2018 | Guy et al. |
| 10,092,525 B2 | 10/2018 | Guy et al. |
| 10,111,840 B2 | 10/2018 | Guy et al. |
| 10,137,095 B2 | 11/2018 | Guy et al. |
| 10,583,096 B2 | 3/2020 | Guy et al. |
| 10,603,288 B2 | 3/2020 | Guy et al. |
| 10,709,671 B2 | 7/2020 | Guy et al. |
| 10,709,673 B2 | 7/2020 | Guy |
| 10,709,674 B2 | 7/2020 | Guy et al. |
| 10,765,643 B2 | 9/2020 | Guy et al. |
| 10,807,777 B2 | 10/2020 | Whittle |
| 10,849,860 B2 | 12/2020 | Guy et al. |
| 10,918,608 B2 | 2/2021 | Guy et al. |
| 10,966,939 B2 | 4/2021 | Guy et al. |
| 11,065,209 B2 | 7/2021 | Guy et al. |
| 11,065,227 B2 | 7/2021 | Stott et al. |
| 11,096,905 B2 | 8/2021 | Guy et al. |
| 11,147,776 B2 | 10/2021 | Stott et al. |
| 11,147,783 B2 | 10/2021 | Stott et al. |
| 11,154,516 B2 | 10/2021 | Guy et al. |
| 11,154,517 B2 | 10/2021 | Guy et al. |
| 11,160,757 B1 | 11/2021 | Wilkhu et al. |
| 11,160,795 B2 | 11/2021 | Guy et al. |
| 11,207,292 B2 | 12/2021 | Guy et al. |
| 11,229,612 B2 | 1/2022 | Wright et al. |
| 11,291,631 B2 | 4/2022 | Shah |
| 11,311,498 B2 | 4/2022 | Guy et al. |

(Continued)

FOREIGN PATENT DOCUMENTS

WO WO-2015193667 A1 12/2015
WO WO-2015193668 A1 12/2015

(Continued)

OTHER PUBLICATIONS

Harvey, D. J., "Characterization of the Butyl Homologues of Delta1-tetrahydrocannabinol, Cannabinol and Cannabidiol in Samples of Cannabis by Combined Gas Chromatography and Mass Spectrometry," J. Pharm. Pharmac., 28:280-285 (1976).
Hill, T. D. M. et al., "Cannabidivarin-rich cannabis extracts are anticonvulsant in mouse and rat via a CB 1 receptor-independent mechanism," British Journal of Pharmacology, 170(3):679-692 (2013).
Morales, P. et al., "An Overview on Medicinal Chemistry of Synthetic and Natural Derivatives of Cannabidiol," Frontiers in Pharmacology, 8:422 (2017); doi:10.3389/fphar.2017.00422, 18 pages.
Epidiolex® (cannabidiol) oral solution, CV, Prescribing Information, 2018, 30 pages; https://www.accessdata.fda.gov/drugsatfda_docs/label/2018/210365lbl.pdf.

(Continued)

*Primary Examiner* — Sahar Javanmard
(74) *Attorney, Agent, or Firm* — COOLEY LLP

(57) ABSTRACT

The present invention relates to a cannabidiol (CBD) type cannabinoid compound for use as a medicament. The CBD-type cannabinoid, 6-hydroxy cannabidiol (6-0 H CBD), is a metabolite of CBD. The cannabinoid can be produced by synthetic means and a method for the production of 6-0 H CBD is described herein. In addition, disclosed herein are data which demonstrate the efficacy of 6-0 H CBD in a model of disease.

10 Claims, 2 Drawing Sheets

(56) References Cited

U.S. PATENT DOCUMENTS

| | | |
|---|---|---|
| 11,357,741 B2 | 6/2022 | Guy et al. |
| 11,400,055 B2 | 8/2022 | Guy et al. |
| 11,406,623 B2 | 8/2022 | Guy et al. |
| 11,419,829 B2 | 8/2022 | Whalley et al. |
| 11,426,362 B2 | 8/2022 | Wright et al. |
| 11,446,258 B2 | 9/2022 | Guy et al. |
| 11,590,087 B2 | 2/2023 | Guy et al. |
| 11,633,369 B2 | 4/2023 | Guy et al. |
| 11,679,087 B2 | 6/2023 | Guy et al. |
| 11,684,598 B2 | 6/2023 | Stott et al. |
| 11,701,330 B2 | 7/2023 | Guy et al. |
| 11,766,411 B2 | 9/2023 | Guy et al. |
| 11,793,770 B2 | 10/2023 | Stott et al. |
| 11,806,319 B2 | 11/2023 | Wilkhu et al. |
| 11,865,102 B2 | 1/2024 | Guy et al. |
| 11,963,937 B2 | 4/2024 | Guy |
| 12,023,305 B2 | 7/2024 | Whalley et al. |
| 12,064,398 B2 | 8/2024 | Wright et al. |
| 12,064,399 B2 | 8/2024 | Guy et al. |
| 12,102,619 B2 | 10/2024 | Guy et al. |
| 2014/0298511 A1 | 10/2014 | Lewis et al. |
| 2015/0359756 A1 | 12/2015 | Guy et al. |
| 2017/0239193 A1 | 8/2017 | Guy et al. |
| 2018/0071210 A1 | 3/2018 | Wilkhu et al. |
| 2018/0228751 A1 | 8/2018 | Stott et al. |
| 2019/0167583 A1 | 6/2019 | Shah |
| 2019/0314296 A1 | 10/2019 | Wright et al. |
| 2019/0321307 A1 | 10/2019 | Guy et al. |
| 2019/0365667 A1 | 12/2019 | Wright et al. |
| 2020/0138738 A1 | 5/2020 | Guy et al. |
| 2020/0179303 A1 | 6/2020 | Guy et al. |
| 2020/0206153 A1 | 7/2020 | Whalley et al. |
| 2020/0237683 A1 | 7/2020 | Whalley et al. |
| 2020/0297656 A1 | 9/2020 | Guy et al. |
| 2020/0352878 A1 | 11/2020 | Guy et al. |
| 2021/0015789 A1 | 1/2021 | Guy et al. |
| 2021/0052512 A1 | 2/2021 | Guy et al. |
| 2021/0059949 A1 | 3/2021 | Wilkhu et al. |
| 2021/0059960 A1 | 3/2021 | Wilkhu et al. |
| 2021/0059976 A1 | 3/2021 | Wilkhu et al. |
| 2021/0169824 A1 | 6/2021 | Guy et al. |
| 2021/0177773 A1 | 6/2021 | Guy et al. |
| 2021/0290565 A1 | 9/2021 | Guy et al. |
| 2021/0330636 A1 | 10/2021 | Guy et al. |
| 2021/0401771 A1 | 12/2021 | Guy et al. |
| 2022/0000800 A1 | 1/2022 | Guy et al. |
| 2022/0008355 A1 | 1/2022 | Guy et al. |
| 2022/0016048 A1 | 1/2022 | Guy et al. |
| 2022/0023232 A1 | 1/2022 | Guy et al. |
| 2022/0040155 A1 | 2/2022 | Guy et al. |
| 2022/0062197 A1 | 3/2022 | Stott et al. |
| 2022/0062211 A1 | 3/2022 | Stott et al. |
| 2022/0087951 A1 | 3/2022 | Knappertz |
| 2022/0096397 A1 | 3/2022 | Wright et al. |
| 2022/0168266 A1 | 6/2022 | Guy et al. |
| 2022/0183997 A1 | 6/2022 | Guy et al. |
| 2022/0184000 A1 | 6/2022 | Guy et al. |
| 2022/0202738 A1 | 6/2022 | Guy et al. |
| 2022/0211629 A1 | 7/2022 | Wilkhu et al. |
| 2022/0226257 A1 | 7/2022 | Guy et al. |
| 2022/0249396 A1 | 8/2022 | Guy et al. |
| 2022/0257529 A1 | 8/2022 | Guy et al. |
| 2022/0265573 A1 | 8/2022 | Guy et al. |
| 2022/0288055 A1 | 9/2022 | Silcock et al. |
| 2022/0378714 A1 | 12/2022 | Guy et al. |
| 2022/0395471 A1 | 12/2022 | Guy et al. |
| 2023/0022487 A1 | 1/2023 | Guy et al. |
| 2023/0024312 A1 | 1/2023 | Whalley et al. |
| 2023/0026079 A1 | 1/2023 | Guy et al. |
| 2023/0032502 A1 | 2/2023 | Guy et al. |
| 2023/0038423 A1 | 2/2023 | Silcock et al. |
| 2023/0068885 A1 | 3/2023 | Guy et al. |
| 2023/0143812 A1 | 5/2023 | Knappertz et al. |
| 2023/0235825 A1 | 7/2023 | Thompson et al. |
| 2023/0248664 A1 | 8/2023 | Guy |
| 2023/0263744 A1 | 8/2023 | Guy et al. |
| 2023/0277560 A1 | 9/2023 | Checketts et al. |
| 2023/0277561 A1 | 9/2023 | Checketts et al. |
| 2023/0277562 A1 | 9/2023 | Checketts et al. |
| 2023/0277563 A1 | 9/2023 | Checketts et al. |
| 2023/0285419 A1 | 9/2023 | Checketts et al. |
| 2023/0285420 A1 | 9/2023 | Checketts et al. |
| 2023/0285421 A1 | 9/2023 | Checketts et al. |
| 2023/0285422 A1 | 9/2023 | Checketts et al. |
| 2023/0285423 A1 | 9/2023 | Checketts et al. |
| 2023/0285424 A1 | 9/2023 | Checketts et al. |
| 2023/0285425 A1 | 9/2023 | Checketts et al. |
| 2023/0285426 A1 | 9/2023 | Checketts et al. |
| 2023/0285427 A1 | 9/2023 | Checketts et al. |
| 2023/0285428 A1 | 9/2023 | Checketts et al. |
| 2023/0301934 A1 | 9/2023 | Whalley et al. |
| 2023/0301936 A1 | 9/2023 | Guy et al. |
| 2023/0310464 A1 | 10/2023 | Checketts et al. |
| 2023/0346809 A1 | 11/2023 | Craig |
| 2023/0372367 A1 | 11/2023 | Checketts et al. |
| 2023/0372368 A1 | 11/2023 | Checketts et al. |
| 2024/0016819 A1 | 1/2024 | Craig |
| 2024/0025858 A1 | 1/2024 | Silcock et al. |
| 2024/0033229 A1 | 2/2024 | Guy et al. |
| 2024/0033272 A1 | 2/2024 | Checketts et al. |
| 2024/0043388 A1 | 2/2024 | Silcock et al. |
| 2024/0050452 A1 | 2/2024 | Craig et al. |
| 2024/0091241 A1 | 3/2024 | Guy et al. |
| 2024/0130981 A1 | 4/2024 | Wilkhu |
| 2024/0131041 A1 | 4/2024 | Tse |
| 2024/0165048 A1 | 5/2024 | Guy |
| 2024/0207220 A1 | 6/2024 | Guy et al. |
| 2024/0215910 A1 | 7/2024 | Tse et al. |
| 2024/0226032 A9 | 7/2024 | Wilkhu et al. |
| 2024/0226123 A9 | 7/2024 | Tse |
| 2024/0238218 A1 | 7/2024 | Silcock et al. |
| 2024/0254066 A1 | 8/2024 | Silcock et al. |
| 2024/0254072 A1 | 8/2024 | Silcock et al. |
| 2024/0261234 A1 | 8/2024 | Guy |
| 2024/0293762 A1 | 9/2024 | Loft et al. |

FOREIGN PATENT DOCUMENTS

| | | |
|---|---|---|
| WO | WO-2016094810 A2 | 6/2016 |
| WO | WO-2016203239 A1 | 12/2016 |
| WO | WO-2018061007 A1 | 4/2018 |
| WO | WO-2018205022 A1 | 11/2018 |

OTHER PUBLICATIONS

Gaston, T. E. & Szaflarski, J. P., "Cannabis for the Treatment of Epilepsy: an Update," Current Neurology and Neuroscience Reports, 18:73 (2018); doi:10.1007/s11910-018-0882-y.

Kimball, A. W. et al., Chemical Protection against Ionizing Radiation, Radiation Research, 7:1-12 (1957).

Lander, N. et al., "Total Syntheses of Cannabidiol and Δ1-Tetrahydrocannabiinol Metabolites," J Chem Soc Perkin 1, (1):8-16 (1976).

Lewis, M. M. et al., Chemical Profiling of Medical Cannabis Extracts, ACS Omega, 2:6091-6103 (2017).

Litchfield, J. T. & Wilcoxon, F., A simplified method of evaluating dose-effect experiments, J Pharmacol Exp Ther, 96(2):99-113 (1949).

Loscher, W. et al., The role of technical, biological and pharmacological factors in the laboratory evaluation of anticonvulsant drugs. II. Maximal electroshock seizure models, Epilepsy Res., 8:79-94 (1991).

Pertwee, R. G., "The Pharmacology and Therapeutic Potential of Cannabidiol," Cannabinoids, Chapter 3, DiMarzo, V. (Ed.), pp. 32-83 (2004).

Swinyard, E. A. & Kupferberg, H. J., "Antiepileptic drugs: detection, quantification, and evaluation," Federation Proceedings, 44(10):2629-2633 (1985).

Ujávry, I. & Hanus, L., "Human Metabolites of Cannabidiol: A Review on Their Formation, Biological Activity, and Relevance in Therapy," Cannabis and Cannabinoid Research, 1(1):90-101 (2016); doi:10.1089/can.2015.0012.

Figure 1. Effect of 6-OH Cannabidiol (6-OH CBD) on the electroshock-induced generalised seizure threshold (MEST) in the mouse
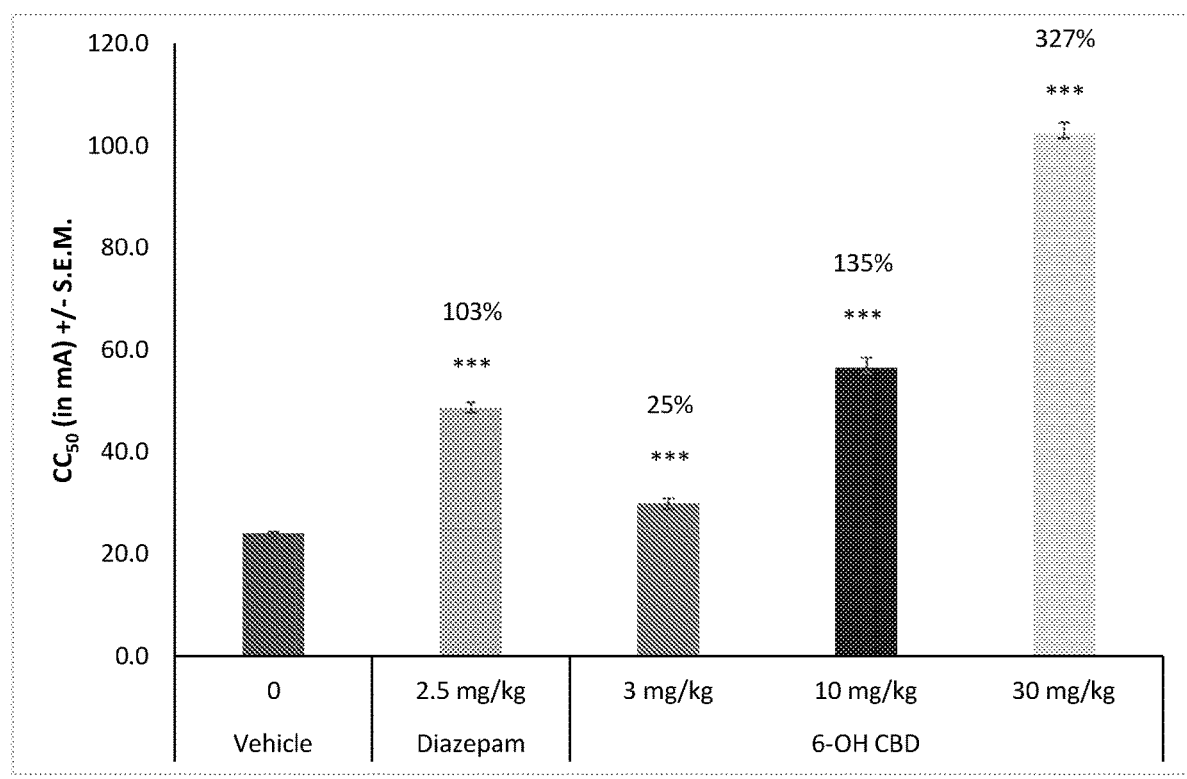
* $P<0.05$;  $P<0.01$; * $P<0.001$ Significant change in threshold when compared to own vehicle Figure 2. Pharmacokinetics of 6-OH Cannabidiol (6-OH CBD) in plasma and brain of mice following a single intravenous or intraperitoneal administration
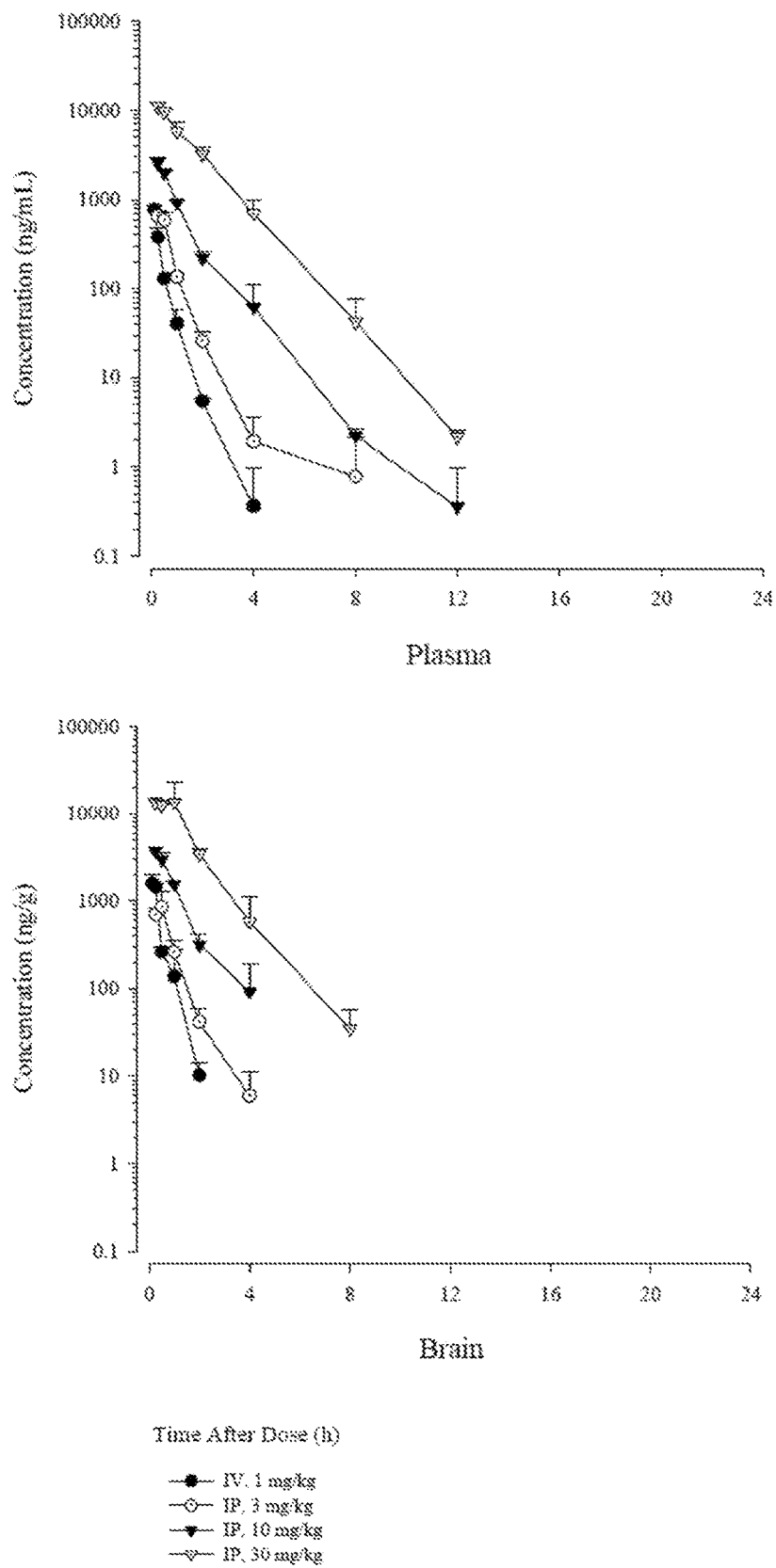

CANNABIDIOL-TYPE CANNABINOID COMPOUND

FIELD OF THE INVENTION

The present invention relates to a cannabidiol (CBD) type cannabinoid compound for use as a medicament.

The CBD-type cannabinoid, 6-hydroxy cannabidiol (6-OH CBD), is a metabolite of CBD.

The cannabinoid can be produced by synthetic means.

Disclosed herein are data which demonstrate the efficacy of 6-OH CBD in a model of disease. In addition, a method for the production of 6-OH CBD is described.

BACKGROUND TO THE INVENTION

Cannabinoids are natural and synthetic compounds structurally or pharmacologically related to the constituents of the cannabis plant or to the endogenous agonists (endocannabinoids) of the cannabinoid receptors CB1 or CB2. The only way in nature in which these compounds are produced is by the cannabis plant. *Cannabis* is a genus of flowering plants in the family Cannabaceae, comprising the species *Cannabis sativa*, *Cannabis indica*, and *Cannabis ruderalis* (sometimes considered as part of *Cannabis sativa*).

*Cannabis* plants comprise a highly complex mixture of compounds. At least 568 unique molecules have been identified. Among these compounds are cannabinoids, terpenoids, sugars, fatty acids, flavonoids, other hydrocarbons, nitrogenous compounds, and amino acids.

Cannabinoids exert their physiological effects through a variety of receptors including, but not limited to, adrenergic receptors, cannabinoid receptors (CB1 and CB2), GPR55, GPR3, or GPR5. The principle cannabinoids present in *Cannabis* plants are cannabinoid acids Δ9-tetrahydrocannabinolic acid (Δ9-THCA) and cannabidiolic acid (CBDA) with small amounts of their respective neutral (decarboxylated) cannabinoids. In addition, *Cannabis* may contain lower levels of other minor cannabinoids. "Chemical composition, pharmacological profiling, and complete physiological effects of these medicinal plants, and more importantly the extracts from *Cannabis*, remain to be fully understood." Lewis, M. M. et al., ACS Omega, 2, 6091-6103 (2017).

Crude extracts from *Cannabis* plants containing CBD have been used by patients suffering from diseases and disorders. However, such crude products are unsuitable for use in pharmaceutical formulations. Those seeking to prepare more consistent CBD preparations for use in treating diseases or disorders have made a concerted effort to either prepare CBD synthetically or attempt to remove all compounds other than CBD, particularly psychoactive compounds such as THC, from plant derived cannabinoids. See for example US 2014/0298511.

The present invention encompasses the surprising discovery that a metabolite of CBD has therapeutic efficacy. This compound, 6-hydroxy cannabidiol (6-OH CBD) can be produced synthetically and may be used in a purified form.

Cannabinoids are a class of compounds which many of which can be derived naturally from the cannabis plant or produced synthetically via chemical synthesis.

More than 100 different cannabinoids produced by *Cannabis* have been identified. These cannabinoids can be split into different groups as follows: phytocannabinoids; endocannabinoids and synthetic cannabinoids (which may be novel cannabinoids or synthetically produced versions of phytocannabinoids or endocannabinoids).

Phytocannabinoids are cannabinoids that originate from nature and can be found in the *Cannabis* plant. Phytocannabinoids can be isolated from plants to produce a highly purified extract. Phytocannabinoids may be obtained as either the neutral (decarboxylated form) or the carboxylic acid form depending on the method used to extract the cannabinoids from plant material. For example, it is known that heating the carboxylic acid form will cause most of the carboxylic acid form to decarboxylate into the neutral form. Phytocannabinoids can only be produced from plants, however versions of phytocannabinoids may be produced synthetically via chemical synthesis.

Endocannabinoids are endogenous lipid-based retrograde neurotransmitters that bind to cannabinoid receptors, and cannabinoid receptor proteins that are expressed throughout the mammalian central nervous system (including the brain) and peripheral nervous system. The endocannabinoid system is involved in regulating a variety of physiological and cognitive processes including fertility, pregnancy, during pre- and postnatal development, appetite, pain-sensation, mood, and memory, and in mediating the pharmacological effects of *Cannabis*.

Synthetic cannabinoids are compounds that have a cannabinoid-like structure and are manufactured using chemical means rather than by the plant.

Certain cannabinoids are described in more detail below.

Cannabidiol (CBD) is a major cannabinoid constituent of *Cannabis* species, such as the hemp plant (*Cannabis sativa*). Unlike other cannabinoids, such as THC, cannabidiol does not bind CB1 or CB2, or its binding to the receptors is negligible in terms of inducing a pharmacological effect. Thus, cannabidiol does not cause the central or peripheral nervous system effects mediated by the CB1 or CB2 receptors. CBD has little or no psychotropic (cannabimimetic) activity and its molecular structure and properties are substantially different from those of other cannabinoids.

Cannabidiol administration has been the subject of research in an attempt to provide an alternative treatment for various diseases and disorders which may respond to such treatment.

There have been many studies done in animals to determine the metabolism of CBD. The pharmacokinetics of CBD are complex, mainly due to a substantial first pass effect. This in turn causes the bioavailability of oral CBD to be poor in humans and other species.

The most abundant metabolites of CBD are hydroxylated 7-carboxy derivatives of CBD which include: 2"-OH-7-COOOH,3",4",5"-trinor CBD; CBD-glucuronide; 4"-OH-7-COOH CBD; 2"-OH-7-COOH CBD; 10-OH-7-COOH CBD; 3"-OH-7-COOH CBD; 7-OH-3"-COOH,4",5"-dinor CBD; 7-COOH-8,9-dihydro-8,9-diOH CBD; 1"-OH-7-COOH CBD; 6-OH-42-COOH,5"-nor CBD; 6-OH-3"-COOH,4",5"-dinor CBD; 7-COOH CBD; 7-OH-4"-COOH, 5"-nor CBD; 4"-COOH,5"-nor CBD; 7-OH CBD; 8,9-dihydro-7,8,9-triOH CBD; cannabinol; 3"-COOH,4",5"-dinor CBD; 2"-COOH,3",4",5"-trinor CBD; 2",6-diOH,3", 4",5"-trinor CBD6,7-diOH CBD; 7-OH-1"-COOH,2",3",4", 5"-tetranor CBD; 6-OH CBD; 7-OH-5"-COOH CBD; 1"-COOH,2",3",4",5"-tetranor CBD; 6-OH-1"-COOH,2", 3",4",5"-tetranor CBD and 6-OH-5"-COOH CBD (Ujvary and Hanus, 2016).

The U.S. Pat. No. 6,630,507 describes numerous analogues of cannabidiol. The compound 6-OH CBD is detailed in the document however there are no data presented to provide evidence that this compound may have any efficacy as a therapeutic agent.

Tetrahydrocannabinol (THC) is the principal psychoactive constituent of cannabis. THC is a partial agonist at the CB1 and CB2 receptors. Synthetic THC or dronabinol is approved for the treatment of loss of appetite in AIDS patients and nausea and vomiting caused by cancer chemotherapy.

Of the over 100 natural cannabinoids identified in *Cannabis sativa*, seven have been classified as CBD-type compounds, these cannabinoids have the same absolute configuration as CBD. These are: CBD, Cannabidiolic acid (CBDA), Cannabidivarin (CBDV), Cannabidivarin acid (CBDVA), Cannabidiol-C1 (CBD-C1), Cannabidiol-C4 (CBD-C4), Cannabidiol-C6 (CBD-C6) and Cannabidiol monomethyl ether (CBDM).

Cannabidiolic acid (CBDA) is the main form in which CBD exists in the cannabis plant. It is converted into CBD after decarboxylation.

Cannabidivarin (CBDV) is a homolog of CBD, with the sidechain shortened by two methylene bridges. CBDV is a non-psychoactive cannabinoid and has been shown to have anti-convulsant activity in a mouse model of epilepsy.

Cannabidiol-C1 (CBD-C1) also known as cannabidiorcol is a homolog of CBD, with the sidechain shortened by four methylene bridges. CBD-C1 occurs naturally in plants producing CBD but has not been shown to have any therapeutic effects.

Cannabidiol-C4 (CBD-C4) also known as nor-cannabidiol is a homolog of CBD, with the sidechain shortened by one methylene bridge. CBD-C4 occurs naturally in plants producing CBD and prior to the present invention has not been shown to have any therapeutic effects.

Cannabidiol-C6 (CBD-C6) is a homolog of CBD, with the sidechain increased by one methylene bridge. CBD-C6 may occur naturally in plants producing CBD and prior to the present invention has not been shown to have any therapeutic effects.

The present invention demonstrates data for the first time to indicate that the compound 6-hydroxy cannabidiol may have therapeutic benefit.

BRIEF SUMMARY OF THE DISCLOSURE

In accordance with a first aspect of the present invention there is provided 6-hydroxy cannabidiol (6-OH CBD) for use as a medicament.

Preferably the 6-OH CBD is present as a synthetic compound. Alternatively, the 6-OH CBD is present as a pure and isolated compound.

Preferably the dose of 6-OH CBD is greater than 100 mg/kg/day. More preferably the dose of 6-OH CBD is greater than 250 mg/kg/day. More preferably the dose of 6-OH CBD is greater than 500 mg/kg/day. More preferably the dose of 6-OH CBD is greater than 750 mg/kg/day. More preferably the dose of 6-OH CBD is greater than 1000 mg/kg/day. More preferably the dose of 6-OH CBD is greater than 1500 mg/kg/day.

Alternatively, the dose of 6-OH CBD is less than 100 mg/kg/day. More preferably the dose of 6-OH CBD is less than 50 mg/kg/day. More preferably the dose of 6-OH CBD is less than 20 mg/kg/day. More preferably the dose of 6-OH CBD is less than 10 mg/kg/day. More preferably the dose of 6-OH CBD is less than 5 mg/kg/day. More preferably the dose of 6-OH CBD is less than 1 mg/kg/day. More preferably the dose of 6-OH CBD is less than 0.5 mg/kg/day.

In accordance with a second aspect of the present invention there is provided a composition for use as a medicament comprising 6-hydroxy cannabidiol (6-OH CBD), and one or more pharmaceutically acceptable excipients.

In accordance with a third aspect of the present invention there is provided a 6-hydroxy cannabidiol (6-OH CBD) for use in the treatment of epilepsy. Preferably the epilepsy is treated in a mammal. More preferably the mammal is a human. Alternatively, the mammal is a dog.

In accordance with a fourth aspect of the present invention there is provided a method for the production of 6-hydroxy cannabidiol.

BRIEF DESCRIPTION OF THE DRAWINGS

Embodiments of the invention are further described hereinafter with reference to the accompanying drawings, in which:

FIG. 1 shows the effect of 6-OH CBD in the MEST test in mouse.

FIG. 2 shows the pharmacokinetics of 6-OH CBD in plasma and brain of mice following a single intravenous or intraperitoneal administration.

Cannabinoids And Their Abbreviations

The cannabinoids described in the present application are listed below along with their standard abbreviations.

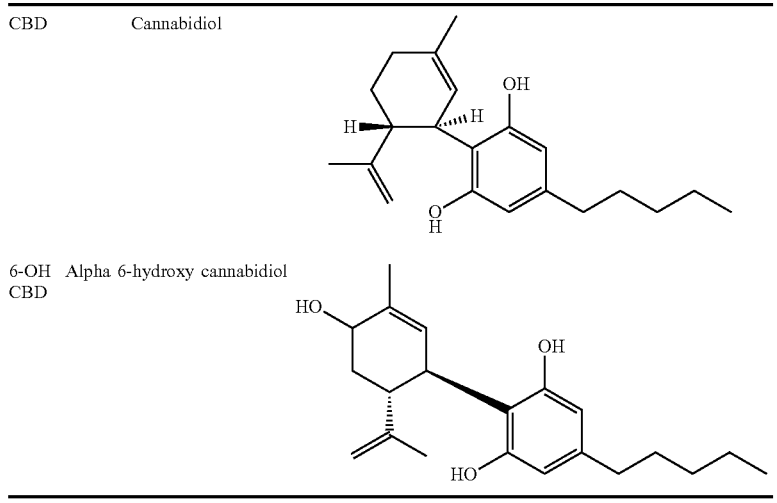

| CBD | Cannabidiol |
| --- | --- |
| 6-OH CBD | Alpha 6-hydroxy cannabidiol |

DETAILED DESCRIPTION

Example 1: Synthetic Production Method for Alpha 6-Hydroxy Cannabidiol (6-OH CBD)

The compound 6-OH CBD is a known metabolite of cannabidiol.

The synthetic pathway described below details a methodology that can be used in order to produce the cannabinoid alpha 6-OH CBD.

On the scheme R=$C_5H_{11}$

To cannabidiol (5.00 g, 15.8 mmol) in anhydrous pyridine (20 mL) was added acetic anhydride (5.13 g, 4.75 mL, 50.2 mmol) and the solution was stirred for 4 h. Dichloromethane (300 mL) was added and the solution was washed with water (200 ml), 1M hydrochloric acid (200 mL), saturated aqueous sodium bicarbonate (200 mL), dried (MgSO4) and concentrated to give cannabidiol diacetate (5.72 g, quantitative), as a straw yellow oil which was used without further purification.

To cannabidiol diacetate (6.18 g, 15.5 mmol) in glacial acetic acid (14 mL) and acetic anhydride (7.12 g, 6.59 mL, 69.8 mmol) was added sodium dichromate (4.87 g, 18.6 mmol) and the mixture was stirred at room temperature for 4 days. The resulting solution was diluted with water (200 mL) and extracted with diethyl ether (200 mL followed by 150 mL). The combined organic layers were washed with saturated aqueous sodium bicarbonate (2×100 mL), dried (MgSO4) and concentrated to give a yellow oil that was purified using a Biotage Isolera automated chromatography system under normal phase conditions (silica column, gradient of 5→32% ethyl acetate in petrol) with detection at 254 nm to give 6-oxo-cannabidiol diacetate (2.03 g 33%), as a colourless oil.

Rf=0.45 (ethyl acetate-petrol, 1:4 v/v)

To lithium aluminium hydride (355 mg, 9.37 mmol) in diethyl ether (36 mL) at 0° C. was added 6-oxo-cannabidiol diacetate (0.92 g, 2.23 mmol) in diethyl ether (8 mL) and the mixture was stirred at room temperature for 4 h. The resulting mixture was cooled in an ice bath and cautiously quenched with water (10 mL) dropwise. 1 M Hydrochloric acid (60 mL) was added and the mixture was extracted with diethyl ether (100 mL). The organic layer was washed with saturated brine (80 mL), dried (MgSO4) and concentrated to give a pale yellow oil that was purified using a Biotage Isolera automated chromatography system under normal phase conditions (silica column, gradient of 7→47% ethyl acetate in petrol) with detection at 254 nm to afford 6-oxo-cannabidiol (0.51 g, 69%), as a white glassy solid.

Rf=0.34 (ethyl acetate-petrol, 3:7 v/v)

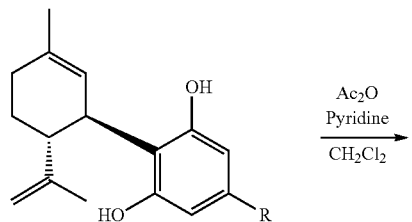

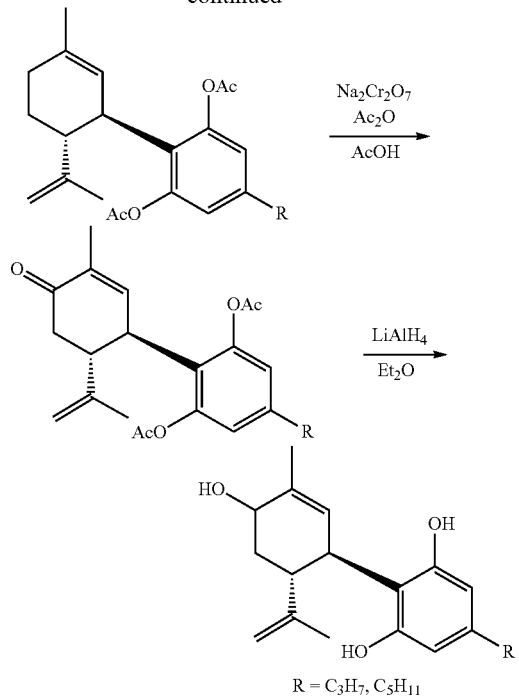

R = $C_3H_7$, $C_5H_{11}$

The resultant material was confirmed to be alpha 6-hydroxy-cannabidiol (6-OH CBD). The compound is a yellow glassy semi-solid material with the chemical formula $C_{21}H_{30}O_3$ and a molecular weight of 330.5 g/mol.

Purity of the compound was tested by HPLC which was shown to produce a 95.6% pure material.

6-OH CBD was stored at −20° C. and protected from light until required for testing.

Example 2: Evaluation of 6-Hydroxy CannabidioL (6-OH CBD) for Anticonvulsant Activity Using the Supramaximal Electroshock Seizure (MES) Test in the Mouse The efficacy of 6-OH CBD was tested in a mouse model of seizure, the supramaximal electroshock seizure (MES) test.

The supramaximal electroshock seizure (MES) test is widely utilized preclinically to evaluate anti-convulsant properties of molecules and standard anti-epileptic drugs (Loscher et al., 1991).

The MES test is a very stringent model in which mice receive a predetermined high-level electrical stimulus of sufficient intensity to reliably produce tonic hindlimb extensor seizures in 100% of control animals. As such the MES test is a rigorous evaluation of anticonvulsant activity (Swinyard, 1985).

Methods

Naïve mice were acclimatised to the procedure room in their home cages, with food and water available ad libitum.

Animals were dosed i.p. according to treatment group.

The vehicle (10 ml/kg i.p. 60 min pre-treatment time) was 1:1:18 vehicle 5% ethanol, 5% kolliphor EL, 90% saline.

The test compound, alpha 6-OH CBD was prepared according to the method described in Example 1.

The test compound, 6-OH CBD was administered at doses of 3, 30, 100 and 200 mg/kg given at 10 ml/kg i.p. 60 min pre-treatment time.

In addition, a dose of 100 mg/kg CBD was given at 10 ml/kg i.p. at 120 minutes pre-treatment time to assess the effect of the drug over a longer time course.

The positive control valproate was used at 250 mg/kg (10 ml/kg i.p. 30 min pre-treatment time).

Mice were individually assessed for the production of a tonic hind limb extensor seizure following a pre-determined high level (30 mA: 50 Hz) corneally delivered electroshock (0.2 sec duration) of sufficient intensity to reliably produce tonic hindlimb seizures in 100% of control animals.

Induction of seizure is measured as an all-or-nothing effect scored as either present (+) or absent (0) for each animal.

Data was collected by an observer unaware of the treatment for each animal and was expressed as the number of +'s or 0's for each treatment group.

The percentage inhibition of relevant vehicle treated group (the protection relative to vehicle treated controls) was then generated.

Significant differences between individual treatment groups and vehicle-treated groups were assessed using 2-tailed Fisher's Exact Probability test ($p<0.05$ considered significant).

Results

Table 1 below demonstrates the data produced in this experiment.

In the positive control valproate (250 mg/kg) treated group, administered i.p. 30 minutes before the test, all animals were scored as not having a seizure. This result was statistically significant ($p<0.001$) compared to the vehicle control.

In the 6-OH CBD treatment groups, administered i.p. 120 minutes before the test, the dose of 3 mg/kg 6-OH CBD was ineffective. However, the doses of 30, 100 and 200 mg/kg 6-OH CBD enabled all mice within the group to withstand seizures and produced a statistically significant effect compared to vehicle ($p<0.001$).

In addition, the dose of 6-OH CBD (100 mg/kg) given 120 minutes also produced a statistically significant reduction of seizures compared to the vehicle control.

TABLE 1

Evaluation of effect of 6-OH CBD in the MES test

| Treatment | Dose (mg/kg) | N | Pre-treatment time (mins) | % change from vehicle | Significance |
|---|---|---|---|---|---|
| Vehicle | — | 10 | 60 | — | — |
| Valproate | 250 | 10 | 30 | 100% | P < 0.001 |
| 6-OH CBD | 3 | 10 | 60 | 0% | — |
| 6-OH CBD | 30 | 10 | 60 | 100% | P < 0.001 |
| 6-OH CBD | 100 | 10 | 60 | 100% | P < 0.001 |
| 6-OH CBD | 200 | 10 | 60 | 100% | P < 0.001 |
| 6-OH CBD | 100 | 10 | 120 | 100% | P < 0.001 |

Conclusions

These data demonstrate for the first time a therapeutic effect for the compound 6-OH CBD.

The data showing the 6-OH CBD given 2 hours (120 minutes) before the mice received the electroshock demonstrates that the compound was able to have a long-lasting effect.

These data are significant as they provide heretofore unknown evidence that this cannabinoid may be of therapeutic value.

Example 3: Evaluation of 6-Hydroxy Cannabidiol (6-OH CBD) for Anticonvulsant Activity Using the Maximal Electroshock Seizure Threshold (MEST) Test in the Mouse The efficacy of 6-OH CBD was tested in a mouse model of generalised seizure, the maximal electroshock seizure threshold (MEST) test.

The maximal electroshock seizure threshold (MEST) test is widely utilized preclinically to evaluate pro- or anti-convulsant properties of test compounds (Loscher et al., 1991).

In the MEST test the ability of a drug to alter the seizure threshold current required to induce hind limb tonic extensor convulsions is measured according to an "up and down" method of shock titration (Kimball et al., 1957). An increase in seizure threshold is indicative of anti-convulsant effect. Antiepileptic drugs including the sodium channel blockers (e.g. lamotrigine) with clinically proven efficacy against generalised tonic-clonic seizures all exhibit anti-convulsant properties in this test in the mouse.

Conversely, a reduction in seizure threshold is indicative of a pro-convulsant effect as observed with known convulsant agents such as picrotoxin.

The ability of a test compound to alter the stimulus intensity, expressed as current (mA), required to induce the presence of tonic hind limb extensor convulsions, is assessed in the MEST. The outcome of the presence (+) or absence (0) of tonic hind limb extensor convulsions observed from a current to produce tonic hind limb extension in 50% of animals in the treatment group ($CC_{50}$) determines the seizure threshold for the treatment group and the effects were then compared to the $CC_{50}$ of the vehicle control group.

Methods

Study Details:

Naïve mice were acclimatised to the procedure room in their home cages for up to 7 days, with food and water available ad libitum.

All animals were weighed at the beginning of the study and randomly assigned to treatment groups based on a mean distribution of body weight across groups. All animals were dosed at 10 mL/kg via intraperitoneal (i.p) injection, with either vehicle, test compound at 3, 10 or 30 mg/kg or diazepam at 2.5 mg/kg.

Animals were individually assessed for the production of a tonic hind limb extensor convulsion at 30 min post-dose for vehicle, 30, 15 and 60 min post-dose for 6-OH CBD at 3, 10 and 30 mg/kg respectively, and 30 min post-dose for diazepam, from a single electroshock.

The first animal within a treatment group was given a shock at the expected or estimated $CC_{50}$ current. For subsequent animals, the current was lowered or raised depending on the convulsions outcome from the preceding animal.

Data generated from each treatment group were used to calculate the $CC_{50} \pm SEM$ values for the treatment group.

Test Compounds:

Vehicle: (5% ethanol, 5% solutol, 90% Saline) was prepared as follows: 2 mL of ethanol, 2 mL of solutol were warmed to 60° C., in 36 mL of saline (1:1:18).

Positive control: diazepam was used at 2.5 mg/kg.

The test compound, alpha 6-OH CBD was prepared according to the method described in Example 1. 6-OH CBD was administered at 3, 10 and 30 mg/kg (i.p.) in a 1:1:18 ethanol:solutol:0.9% saline formulation.

Sample Collection:

Each animal was humanely killed immediately after production of a convulsion by destruction of the brain from striking the cranium, followed by the confirmation of permanent cessation of the circulation from decapitation under The Humane Killing of Animals under Schedule 1 to the Animals (Scientific Procedures) Act 1986. Terminal blood and brain collection were performed following decapitation.

Blood was collected in Lithium-heparin tubes and centrifuged at 4° C. for 10 minutes at 1500×g. The resulting plasma was removed (>100 µL) and split into 2 aliquots of 0.5 mL Eppendorf tubes containing 100 µL of ascorbic acid (100 mg/mL) for stabilisation. Brains were removed, washed in saline and halved. Each half was placed into separate 2 mL screw cap cryovials, weighed and frozen on cardice.

Statistical Analysis

The data for each treatment group were recorded as the number of +'s and 0's at each current level employed and this information is then used to calculate the $CC_{50}$ value (current required for 50% of the animals to show seizure behaviour)±standard error.

6-OH CBD effects were also calculated as percentage change in $CC_{50}$ from the vehicle control group.

Significant difference between drug-treated animals and controls were assessed according to Litchfield and Wilcoxon (1949).

Results

Table 2 below demonstrates the data produced in this experiment, and FIG. 1 illustrates these results.

In the vehicle group, the $CC_{50}$ value was calculated to be 24.0 mA.

In the positive control diazepam (2.5 mg/kg) treated group, administered i.p. 30 minutes before the test, the $CC_{50}$ value was 48.8 mA. This result was statistically significant ($p<0.001$) compared to the vehicle control.

In the 6-OH CBD treatment groups, administered i.p. 30, 15, and 60 minutes before the test, the doses of 3, 10 and 30 mg/kg 6-OH CBD produced a statistically significant $CC_{50}$ value compared to vehicle at all three doses of the compound.

Such data are indicative that this compound will be of therapeutic benefit.

Conclusions

6-OH CBD produced a dose-related increase in MEST, which provides evidence that this compound exhibits anti-convulsive properties. Significant effects were observed at 3, 10, and 30 mg/kg, when compared to vehicle.

These data are significant as they provide heretofore unknown evidence that this cannabinoid may be of therapeutic value.

Example 4: Pharmacokinetics of 6-Hydroxy Cannabidiol (6-OH CBD)

The objective of this study was to determine brain and plasma pharmacokinetic parameters of 6-OH CBD following a single intravenous or intraperitoneal administration of 6-OH CBD to the mouse; and to determine brain: plasma concentration ratios for 6-OH CBD.

Methods

Ninety-nine male mice each received a single intravenous or intraperitoneal dose of 6-OH CBD, as detailed below in Table 3.

TABLE 3

Details of dosing

| Dose route | Dose level (mg/kg) | Number of animals |
|---|---|---|
| intravenous | 1 | 27 |
| intraperitoneal | 3 | 27 |
| intraperitoneal | 10 | 27 |
| intraperitoneal | 30 | 27 |

For each formulation, 6-OH CBD was formulated at the required concentration in ethanol: Kolliphor EL (Cremophor EL): 0.9% (w/v) Saline (1:1:18, v/v/v).

Each animal received a single intravenous administration, via a tail vein, at a nominal dose volume of 2 mL/kg or a single intraperitoneal administration at a nominal dose volume of 5 mL/kg.

Following dosing, terminal blood samples were collected from each animal via cardiac puncture, and brains were excised, at each of the following time points:

Intravenous groups: 7, 15 and 30 minutes, 1, 2, 4, 8, 12 and 24 hours;

Intraperitoneal groups: 15 and 30 minutes, 1, 2, 4, 8, 12 and 24 hours.

Blood was collected into tubes containing lithium heparin anticoagulant and centrifuged to prepare plasma. Brain samples were frozen on dry ice, then weighed and stored deep frozen prior to bioanalysis. The remaining carcasses

TABLE 2

Evaluation of effect of 6-OH CBD in the MEST test

| Treatment | Dose (mg/kg) | N | Pre-treatment time (mins) | $CC_{50} \pm$ SEM | % change from vehicle | Significance |
|---|---|---|---|---|---|---|
| Vehicle | — | 12 | 30 | 24.0 ± 0.4 | — | — |
| Diazepam | 2.5 | 12 | 30 | 48.8 ± 1.1 | 103% | P < 0.001 |
| 6-OH CBD | 3 | 12 | 30 | 30.0 ± 1.1 | 25% | P < 0.001 |
| 6-OH CBD | 10 | 12 | 15 | 56.5 ± 2.1 | 135% | P < 0.001 |
| 6-OH CBD | 30 | 12 | 60 | 102.5 ± 2.2 | 327% | P < 0.001 | were discarded. Plasma was stabilised with an equal volume of ascorbic acid solution, then stored deep frozen prior to bioanalysis.

Stabilised plasma samples were analysed to determine the concentrations of 6-OH CBD, using qualified LC-MS/MS methods. The results of these analyses were evaluated to determine non-compartmental pharmacokinetic parameters.

Results

Tables 4 and 5 demonstrate the results obtained in this study, and FIG. 2 illustrates the results. The following parameters were determined:

The following parameters were determined:
$C_{max}$ Maximum concentration observed.
$T_{max}$ Time of maximum observed concentration.
$AUC_{0-t}$ Area under the concentration-time curve from hour 0 to the last quantifiable concentration, estimated by the linear trapezoidal rule.
$AUC_{0-24}$ Area under the concentration-time curve from hour 0 to hour 24, estimated using the linear trapezoidal rule.
$t_{1/2}$ Elimination half-life, determined as $\ln(2)/\lambda z$.
Cl Clearance, calculated (for intravenous doses only) as $Dose/AUC_{0-inf}$.
Vss Volume of distribution, based on the terminal elimination phase, calculated (for intravenous doses only) as $Cl/\lambda z$.
$F_{abs}$ Absolute bioavailability of the intraperitoneal dose.

hours (15 minutes) at each dose level. After reaching $C_{max}$, plasma concentrations declined, with half-life ($t_{1/2}$) values ranging between 0.993 and 1.08 hours and similar across each dose level assessed.

Following IP administration, 6-OH CBD exposure in plasma (as assessed by $C_{max}$ and $AUC_{0-24}$ values) increased with each increase in dose level between 3 and 30 mg/kg. The observed increases in exposure were greater than dose-proportional, with increases of 16.7-fold for $C_{max}$ and 33.2-fold for $AUC_{0-24}$ for a 10-fold increase in dose level.

The absolute bioavailability of 6-OH CBD following IP administration was 52.1%, 75.8% and 173%, at 3, 10 and 30 mg/kg respectively.

After systemic administration, 6-OH CBD appeared in brain, with $T_{max}$ values of 0.117 hours after IV dosing and ranging from 0.250 to 1 hours. After reaching $C_{max}$, 6-OH CBD concentrations declined, with half-life ($t_{1/2}$) values of 0.312 hours following IV administration and ranging between 0.569 and 0.919 hours, with the trend to increase with increasing dose level, following IP administration.

As can be seen from Table 5, following IP administration, 6-OH CBD exposure in brain (as assessed by $C_{max}$ and $AUC_{0-24}$ values) increased with each increase in dose level between 3 and 30 mg/kg. The observed increases in exposure were greater than dose-proportional, with increases of 15.8-fold for $C_{max}$ and 32.6-fold for $AUC_{0-24}$ for a 10-fold increase in dose level.

Brain: plasma ratios for 6-OH CBD $C_{max}$ and $AUC_{0-24}$ ranged from 1.23 to 2.03 for $C_{max}$ and 1.41 to 2.01 for

TABLE 4

Composite pharmacokinetic parameters of 6-OH CBD in the plasma and brain following a single intravenous or intraperitoneal administration

| Matrix | Treatment | Dose Level (mg/kg) | $C_{max}$ (ng/mL) | $T_{max}$ (h) | $AUC_{0-t}$ (h * ng/mL) | $AUC_{0-24}$ (h * ng/mL) | $t_{1/2}$ (h) | $F_{abs}$ (%) | Cl (mL/min/kg) | Vss (L/kg) |
|---|---|---|---|---|---|---|---|---|---|---|
| Plasma | IV | 1 | 775 | 0.117 | 342 | 343 | 0.451 | NA | 48.7 | 1.90 |
|  | IP | 3 | 658 | 0.250 | 533 | 535 | 0.993 | 52.1 | NA | NA |
|  | IP | 10 | 2550 | 0.250 | 2590 | 2600 | 1.08 | 75.8 | NA | NA |
|  | IP | 30 | 11000 | 0.250 | 17700 | 17700 | 0.959 | 173 | NA | NA |
| Brain | IV | 1 | 1580 | 0.117 | 679 | 690 | 0.312 | NA | NA | NA |
|  | IP | 3 | 851 | 0.500 | 756 | 768 | 0.569 | NA | NA | NA |
|  | IP | 10 | 3680 | 0.250 | 3750 | 3940 | 0.706 | NA | NA | NA |
|  | IP | 30 | 13500 | 1.00 | 25000 | 25000 | 0.919 | NA | NA | NA |

TABLE 5

Brain: plasma ratios for 6-OH CBD $C_{max}$ and $AUC_{0-24}$ values following a single intraperitoneal administration of 6-OH CBD

| Dose Route | Dose level (mg/kg) | Brain: Plasma | |
|---|---|---|---|
|  |  | $C_{max}$ | $AUC_{0-24}$ |
| IV | 1 | 2.03 | 2.01 |
| IP | 3 | 1.29 | 1.44 |
| IP | 10 | 1.45 | 1.52 |
| IP | 30 | 1.23 | 1.41 |

As can be seen from Table 4, following intravenous (IV) administration of 6-OH CBD, at a dose level of 1 mg/kg, $T_{max}$ was observed at 0.117 hours (7 minutes) post dose. After reaching $C_{max}$, 6-OH CBD concentrations declined, with a half-life ($t_{1/2}$) of 0.451 hours. Total plasma clearance was 48.7 mL/min/kg and the volume of distribution was 1.90 L/kg.

After intraperitoneal (IP) administration at 3, 10 or 30 mg/kg, 6-OH CBD was absorbed, with $T_{max}$ values of 0.250

$AUC_{0-24}$. Following IP administration, the ratios for both parameters were similar across each of the dose levels assessed. However, the ratios for both parameters were higher following IV compared with IP administration.

CONCLUSION

After intraperitoneal administration, 6-OH CBD was absorbed with $T_{max}$ values of 15 min for all dosed IP; and 7 min for 1 mg/kg IV.

The results of this study provide evidence of good pharmacokinetic parameters (bioavailability, clearance etc.) for the compound 6-OH CBD.

The invention claimed is:

1. A method of treating epilepsy in a subject in need thereof, comprising administering a pharmaceutical composition comprising a therapeutically effective amount of 6-hydroxy cannabidiol (6-OH CBD) as the only active ingredient.

2. The method of claim 1, wherein the 6-OH CBD is in the form of a synthetic compound.

3. The method of claim 1, wherein the 6-OH CBD is in the form of a pure or isolated compound.

4. The method of claim 1, comprising administering a dose of 6-OH CBD that is less than 100 mg/kg/day to 1 mg/kg/day.

5. The method of claim 1, comprising administering a dose of 6-OH CBD that is less than 100 mg/kg/day.

6. The method of claim 1, wherein the pharmaceutical composition comprises one or more pharmaceutically acceptable excipients.

7. The method of claim 1, wherein the subject is a mammal.

8. The method of claim 1, wherein the subject is a human.

9. The method of claim 1, wherein the subject is a dog.

10. The method of claim 1, comprising administering a dose of 6-OH CBD that is from 1 mg/kg/day to about 250 mg/kg/day.

\* \* \* \* \*